United States Patent [19]

Bloomer

[11] Patent Number: 4,975,463

[45] Date of Patent: Dec. 4, 1990

[54] ETHYL(OR METHYL) 4-ACETOXY(OR PROPIONYLOXY)-5,6,7 OR 8-DI(OR TRI-)SUBSTITUTED-2-NAPHTHOATES

[75] Inventor: James L. Bloomer, Philadelphia, Pa.

[73] Assignee: Temple University of the Commonwealth System of Higher Education, Philadelphia, Pa.

[21] Appl. No.: 393,608

[22] Filed: Aug. 14, 1989

Related U.S. Application Data

[63] Continuation-in-part of Ser. No. 320,779, Mar. 8, 1989, abandoned.

[51] Int. Cl.$^5$ .................... C07C 69/76; A01N 37/10
[52] U.S. Cl. .................... 514/533; 524/544; 524/546; 560/56
[58] Field of Search ................ 560/56; 514/533, 544, 514/546

[56] References Cited

PUBLICATIONS

Chemical Abstracts CA111(7):49897x, 1988.
Chemical Abstracts CA111(25):232399a, 1989.
Chemical Abstracts CA72(19):100348z, 1970.
Handford et al., J. Chem. Soc., 3896, (1963).
Loder et al., J. Chem. Soc. 2233, (1957).
Gazzillo, "Synthetic Approaches to the Ring-D Modification of the Aglycone Moiety of the Anticancer Antibiotic 7-(3-Amino-2,3,6-Trideoxy-L-Lyxohexosyloxy)-9-Acetyl-7,8,9,10-Tetrahydro-6,9-Dihydroxy-4-Methoxy-5,12-Naphtacene-quinone", doctoral dissertation (Apr. 27, 1988).
Bell et al., Aust. J. Chem. 18, 1273–1277, (1965).
Rizzacasa et al., Aust. J. Chem. 40, 1737–1743, (1987).
El-Assal et al., J. Chem. Soc. 849–852, (1960).

Primary Examiner—Paul J. Killos
Attorney, Agent, or Firm—Seidel, Gonda, Lavorgna & Monaco

[57] ABSTRACT

Novel antiviral ring-substituted ethyl or methyl 4-acetoxy (or propionyloxy)-2-naphthoates are provided.

17 Claims, No Drawings

ETHYL(OR METHYL) 4-ACETOXY(OR PROPIONYLOXY)-5,6,7 OR 8-DI(OR TRI-)SUBSTITUTED-2-NAPHTHOATES

CROSS-REFERENCE

This is a continuation-in-part of co-pending application Ser. No. 320,779, filed Mar. 8, 1989, now abandoned.

BACKGROUND OF THE INVENTION

The invention relates to the field of antiviral agents, in particular to novel naphthalene derivatives useful as antiviral agents.

SUMMARY OF THE INVENTION

Novel compounds of the formula

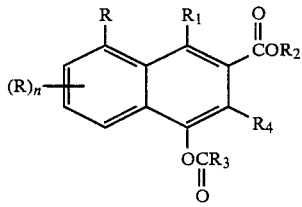
(1)

are provided wherein
n is 1 or 2;
R is methoxy or chloro, or combinations thereof;
$R_1$ is hydrogen or lower alkyl;
$R_2$ is methyl or ethyl;
$R_3$ is methyl or ethyl; and
$R_4$ is hydrogen or methyl.

Compounds wherein $R_4$ is hydrogen are preferred.

The compounds are useful as antiviral agents. The compound ethyl 4-acetoxy-5,8-dimethoxy-2-naphthoate is, in particular, active in inhibiting human immunodeficiency virus ("HIV").

A method of treating mammals for viral infection is provided comprising administering a compound of formula 1, in particular, ethyl 4-acetoxy-5,8-dimethoxy-2-naphthoate, to an infected individual.

A pharmaceutical composition adapted for administration to obtain an antiviral effect comprises an antiviral effective amount of a compound of formula 1 and a pharmaceutical carrier.

DETAILED DESCRIPTION OF THE INVENTION

The compounds of the invention are prepared in two steps from di-substituted or tri-substituted benzaldehydes or aralkyl ketones according to the following scheme wherein n, R, $R_1$, $R_2$, $R_3$ and $R_4$ are defined as above:

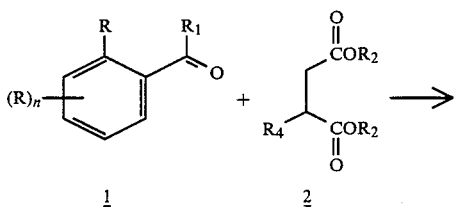

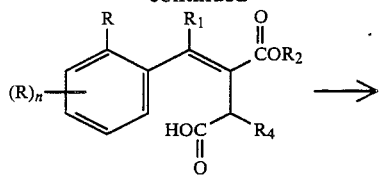

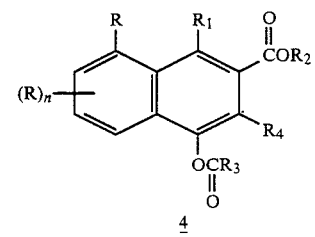

Briefly, for preferred compounds wherein $R_4$ is hydrogen, a di- or tri-substituted benzaldehyde or aralkyl ketone 1 is treated with dimethyl or diethyl succinate 2 in benzene or toluene with sodium hydride and a catalytic amount of ethanol or methanol to yield a di- or tri-substituted 4-phenyl-3-carbomethoxy(or carboethoxy)-3-butenoic acid 3 ($R_1$=H), or 4-alkyl analog thereof ($R_1$=lower alkyl), as an oil. The oil may be taken directly for cyclization with acetic or propionic anhydride in the presence of sodium acetate or sodium propionate, respectively, to provide the ethyl or methyl 4-acetoxy(or propionyloxy)-disubstituted (or trisubstituted)-2-naphthoate 4 ($R_1$=H), or 1-alkyl analog thereof (4, $R_1$=lower alkyl).

Similarly, substitution of diethyl or dimethyl methylsuccinate (2, $R_4$=methyl) in the scheme leads to compounds of the invention wherein $R_4$ is methyl.

The compounds of the invention are useful as antiviral agents.

As used herein, "lower alkyl" means $C_1$ to $C_4$ groups which may contain either a branched or an unbranched chain.

Compounds wherein each R is the same, most preferably wherein each R is methoxy, are preferred. Also preferred are compounds substituted at least at the 5- and 8-positions, that is, compounds of the formula

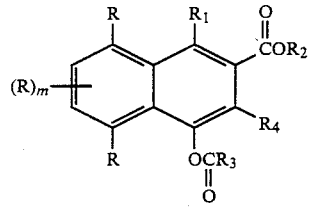

wherein R, $R_1$, $R_2$, $R_3$ and $R_4$ are defined as above, and m is 0 or 1.

The invention is illustrated by the following nonlimiting examples:

EXAMPLE 1

Ethyl 4-acetoxy-5,8-dimethoxy-2-naphthoate

A. 4-(2',5'-Dimethoxyphenyl)-2 carbethoxy 3-butenoic acid. Sodium hydride (2.4 g, 104 mmol) and benzene (50 mL) were stirred under nitrogen. Absolute ethanol (0.5 mL) was added, followed by a dropwise addition of a solution of 2,5-dimethoxybenzaldehyde (6.97 g, 42 mmol) in freshly distilled diethyl succinate (20 mL) at a rate sufficient to maintain a steady evolution of hydrogen and a temperature of approximately 40° C. The mixture was stirred for 1 hour, and acetic acid (10 mL, 175 mmol) was cautiously added, followed by water (20 mL). An ethereal solution of the product was repeatedly washed with an excess of 2N $Na_2CO_3$, and the combined washings were acidified and extracted with ether. The ether layer was dried ($MgSO_4$), filtered, and removed, providing the title compound in 55% yield, mp=110.5°–111.5° C.

UV: 268 (7000), 332 (3500)

$^1$H-NMR: 10.6 (s, 1H), 8.09–7.98, (s, 1H), 6.95–6.8 (m, 3H), 4.3 (q, 2H), 3.78 (s, 3H), 3.76 (s, 3H), 3.63–3.52 (2H), 1.35 (t, 3H).

Anal. Calcd. for $C_{15}H_{18}O_6$: C, 61.21; H, 6.16. Found: C, 61.21; H, 6.14.

B. Ethyl 4-acetoxy-5,8-dimethoxy 2-naphthoate. The crude oil 4-(2',5'-dimethoxyphenyl)-2-carbethoxy-3-butenoic acid (0.1007 g, 0.340 mmol) was treated with 0.2 mL acetic anhydride and 0.030 g sodium acetate (anhydrous), and the reaction mixture was kept in a 140° C. bath for 1.5 hours. The reaction mixture was cooled. Dichloromethane (2 mL), water 1 mL) and sodium carbonate (0.3 g) were added, and the mixture was shaken. The organic layer was dried ($MgSO_4$), and evaporated to give 0.115 g of crude acetoxy ester (about 97%), which could be recrystallized directly from methanol (5 mL) to afford the purified title compound (0.055 g), m.p.=155.0°–155.5° C.

TLC: (Solvent B-) $R_f$=0.74

UV: 241, 313, 348

IR: 2980, 1778, 1713, 1613, 1283, 1258, 1203

$^1$H-NMR ($CDCl_3$): 8.9 (d, J=3 Hz, 1H), 7.7 (d, J=3 Hz, 1H), 6.79 (m, 2H), 4.3 (q, 2H), 3.96 (s, 3H), 3.88 (s, 3H), 2.37 (s, 3H), 1.42 (t, 3H)

$^{13}$C-NMR: 171, 170, 166, 151, 149, 147, 143, 128, 124, 123, 120, 109, 105, 61, 57, 56, 21, 14

MS: 318, 276 (100), 261

Anal. Calcd. for $C_{17}H_{18}O_6$:C, 64.12; H, 5.70 Found: C, 64.17; H, 5.57

EXAMPLE 2

Ethyl 1-methyl 4-acetoxy-5,8-dimethoxy-2-naphthoate

A. 4 (2',5'-dimethoxyphenyl) 3-carboethoxy-4-methyl-3-butenoic acid. Sodium hydride (2.4 g, 104 mmol) and toluene (50 mL) were stirred under nitrogen. Absolute ethanol (0.5 mL) was added, followed by, dropwise, a solution of 2,5-dimethoxyacetophenone (9.01 g, 50 mmol) in freshly distilled diethyl succinate (20 mL) at a rate sufficient to maintain a steady evolution of hydrogen and a temperature of approximately 40° C. The mixture was stirred for 1 hour, and acetic acid (10 mL, 175 mmol) was added, followed by water (20 mL). An ethereal solution of the product was washed with 1M $Na_2CO_3$ (180 mL). The washings were acidified with HCl (50 mL) and extracted with ether. The ether layer was dried ($MgSO_4$), filtered, and evaporated to provide the title compound in 37% yield (5.48 g).

$^1$H-NMR ($CDCl_3$) 1.265–1.349 (3H, m) 2.389 +2.362 (2H, as 2 singlets) 2.105+2.132 (2H, as 2 singlets) 3.741 (3H, s) 3.754 (3H, s) 4.167+4.266 (2H, both as quartets J=7 Hz) 6.567+6.639 (1H as 2 soublets, small J) 6.799+6.834 (complex, appears to have J=10 Hz component) ($CO_2H$ region was not run)

B. Ethyl-1-methyl-4-acetoxy-5,8-dimethoxy-2-naphthoate. The above oil was treated with acetic anhydride 9.24 g (0.09 mol) and sodium acetate (anhydrous) (1.3205 g, 0.02 mol) at 140° for 5 hours. Upon cooling, the mixture solidified. An equal volume of ice was introduced into the flask, whereupon an oil was obtained, which subsequently solidified upon standing overnight. The solid was filtered and air dried. Upon trituration with a 5–10 fold excess of 95% methanol, 3.7764 g of crystals were obtained. After recrystallization from 95% methanol (5–10 fold amount) the m.p. of the title compound was 90°–93° C.

IR: 2930,2620,1760,1708,1610,1220,1140,1045 $cm^{-1}$.(KBr)

$^1$H-NMR ($CDCl_3$): 1.417 (3H, t), 2.368 (3H, s), 2.953 (3H,s), 3.881 (3H, s), 3.890 (3H, s) 6.813–6.881 (2 doublets distorted; appears to have J=9 Hz component) (2H total) 7.309 (1H, s)

EXAMPLE 3

Methyl 4-acetoxy-7,8-dimethoxy2-naphthoate

A. 4-(2',3'-Dimethoxyphenyl)-3-carbomethoxy-3-butenoic acid. Sodium hydride (2.4 g, 104 mmol) and toluene are stirred under nitrogen. Absolute methanol (0.35 mL) is added, followed by dropwise addition of a solution of 2,3-dimethoxybenzaldehyde (6.97 g, 42 mmol) in freshly distilled dimethyl succinate (15.7 mL) at a rate sufficient to maintain a steady evolution of hydrogen and a temperature of 40° C. The mixture is stirred for 1 hour more at 40° C., and then acetic acid (I0 mL) and water (20 mL) are added. The organic layer is extracted with an excess of 2N $Na_2CO_3$, and the washings acidified and extracted with ether. The ether, after drying with $MgSO_4$ and evaporation, affords approximately 55% (23 mmol, 6.44 g) of the title acid as a low-melting solid or oil satisfactory for subsequent cyclization.

B. Methyl 4-acetoxy-7,8-dimethoxy-2-naphthoate. The above acid (0.095 g, 0.340 mmol) is treated with 0.2 mL of acetic anhydride and 0.030 g of sodium acetate (anhydrous), and the stirred reaction mixture is kept in a 140° C. bath for 1.5 hours. The reaction mixture is cooled, and then 2 mL dichloromethane, 1 mL water, and 0.3 g sodium carbonate are added, and the mixture is shaken. The organic layer is dried ($MgSO_4$ ) and evaporated to give the crude bicyclic ester in nearly theoretical yield. Recrystallization from about 5 mL of methanol affords about 51% (0.172 mmol, 0.053 g) of purified title compound as a first crop.

EXAMPLE 4

Methyl-1-methyl-4-acetoxy-6,8-dimethoxy-2-naphthoate

A. 4-(2',4'-Dimethoxyphenyl)-3-carbomethoxy-4-methyl-3-butenoic acid. Sodium hydride (2.4 g, 104 mmol) and toluene are stirred under nitrogen. Absolute ethanol (0.35 mL) is added, followed by dropwise addition of a solution of 2',4'-dimethoxyacetophenone (7.56 g, 42 mmol) in freshly distilled dimethyl succinate (15.7 mL) at a rate sufficient to maintain a steady evolution of hydrogen and a temperature of 40° C. The mixture is stirred for 1 hour more at 40° C., and then acetic acid (10 mL) and water (20 mL) are added. The organic layer is extracted with an excess of 2N $Na_2CO_3$, and the washings acidified and extracted with ether. The ether, after drying with $MgSO_4$ and evaporation, affords approximately 55% (23 mmol, 6.76 g) of the title acid as a low-melting solid or oil satisfactory for subsequent cyclization.

B. Methyl-1-methyl-4-acetoxy-6,8-dimethoxy-2-naphthoate. The above acid (0.100 g, 0.340 mmol) is treated with 0.2 mL of acetic anhydride and 0.030 g of sodium acetate (anhydrous), and the stirred reaction mixture is kept in a 140° C. bath for 1.5 hours. The reaction mixture is cooled, and then 2 mL dichloromethane, 1 mL water, and 0.3 g sodium carbonate are added, and the mixture is shaken. The organic layer is dried (MgSO4) and evaporated to give the crude bicyclic ester in nearly theoretical yield. Recrystallization from about 5 mL of methanol affords about 51% (0.172 mmol, 0.056 g) of purified title compound as a first crop.

EXAMPLE 5

Ethyl 4-acetoxy-5,6,8-trimethoxy-2-naphthoate

A. 4-(2',4',5'-trimethoxyphenyl)-3-carboethoxy-3-butenoic acid. Sodium hydride (2.4 g, 104 mmol) and toluene are stirred under nitrogen. Absolute ethanol (0.5 mL) is added, followed by dropwise addition of a solution of 2,4,5-trimethoxybenzaldehyde (8.23 g, 42 mmol) in freshly distilled diethyl succinate (20 mL) at a rate sufficient to maintain a steady evolution of hydrogen and a temperature of 40° C. The mixture is stirred for 1 hour more at 40° C., and then acetic acid (10 mL) and water (20 mL) are added. The organic layer is extracted with an excess of 2N Na2CO3, and the washings acidified and extracted with ether. The ether, after drying with MgSO4 and evaporation, affords approximately 55% (23 mmol, 7.45 g) of the title acid as a low-melting solid or oil satisfactory for subsequent cyclization.

B. Ethyl-4-acetoxy-5,6,8-trimethoxy-2-naphthoate. The above acid (0.110 g, 0.340 mmol) is treated with 0.2 mL of acetic anhydride and 0.030 g of sodium acetate (anhydrous), and the stirred reaction mixture is kept in a 140° C. bath for 1.5 hours. The reaction mixture is cooled, and then 2 mL dichloromethane, 1 mL water, and 0.3 g sodium carbonate are added, and the mixture is shaken. The organic layer is dried (MgSO4) and evaporated to give the crude bicyclic ester in nearly theoretical yield. Recrystallization from about 5 mL of methanol affords about 51% (0.172 mmol, 0.061 g) of purified title compound as a first crop.

EXAMPLE 6

Ethyl 4-acetoxy-6,7,8-trimethoxy-2-naphthoate

A. 4-(2',3',4'-trimethoxyphenyl)-3-carboethoxy-3-butenoic acid. Sodium hydride (2.4 g, 104 mmol) and toluene are stirred under nitrogen. Absolute ethanol (0.5 mL) is added, followed by dropwise addition of a solution of 2,3,4-trimethoxybenzaldehyde (8.23 g, 42 mmol) in freshly distilled diethyl succinate (20 mL) at a rate sufficient to maintain a steady evolution of hydrogen and a temperature of 40° C. The mixture is stirred for 1 hour more at 40° C., and then acetic acid (10 mL) and water (20 mL) are added. The organic layer is extracted with an excess of 2N Na2CO3, and the washings acidified and extracted with ether. The ether, after drying with MgSO4 and evaporation, affords approximately 55% (23 mmol, 7.45 g) of the title acid as a low-melting solid or oil satisfactory for subsequent cyclization.

B. Ethyl-4-acetoxy-6,7,8-trimethoxy-2-naphthoate. The above acid (0.110 g, 0.340 mmol) is treated with 0.2 mL of acetic anhydride and 0.030 g of sodium acetate (anhydrous), and the stirred reaction mixture is kept in a 140° C. bath for 1.5 hours. The reaction mixture is cooled, and then 2 mL dichloromethane, 1 mL water, and 0.3 g sodium carbonate are added, and the mixture is shaken. The organic layer is dried (MgSO4) and evaporated to give the crude bicyclic ester in nearly theoretical yield. Recrystallization from about 5 mL of methanol affords about 51% (0.172 mmol, 0.061 g) of purified title compound as a first crop.

EXAMPLE 7

Ethyl-4-acetoxy-5,8-dimethoxy-6-chloro-2-naphthoate

A. 4,5-Dimethoxytoluene. To a well-stirred solution of NaOH (44 g, 1.1 mole), and Na2S2O4 (8.7 g, 50 mmol) in water (500 mL) under N2, was added methylhydroquinone (62.07g, 0.50 mole). To the homogeneous solution Me2SO4 (99.4 mL, 1.05 mole) was added and the mixture stirred for 0.5 hour. (If the solution did not remain basic, more NaOH was added, and the mixture stirred for 0.5 hour more). The aqueous layer was extracted with ether (2×200 mL), and the ether layer was washed with 1N NaOH (200 mL). The ether layer was dried (MgSO4), filtered, and the solvent was removed. After vacuum distillation, and the solvent was removed. After vacuum distillation, the yield was 54.9 g, 69%.

TLC: (Solvent B-) $R_f$=0.82

IR: 3010, 2950, 1050

$^1$H-NMR: (300 MHz): 6.86(s,1H), 6.78(s,1H), 3.86(s, 3H), 3.79(s, 3H), 2.21(s, 3H).

B. 4Chloro-2,5-dimethoxytoluene. Sulfuryl chloride (6.69 mL, 83 mmol) was added to 2,5 dimethoxy-toluene (12.68 g, 83 mmol) over a 2.75 hour period at 67° C. The solution was stirred for 15 minutes, then cooled to room temperature. The solid product was dissolved in CH2Cl2 (20 mL) and washed with 10% NaOH (2×20 mL). The CH2Cl2 layer was dried (MgSO4), filtered, and evaporated. Recrystallization from high boiling petroleum ether provided 4-chloro- 2,5-dimethoxytoluene in 56% yield, mp 90°–92° C., (lit.) 92°–93° C.

IR: 3000, 2950, 1040

NMR: 6.82(s, 1H), 6.73(s, 1H), 3.80(s, 3H), 3.73 (s, 3H), 2.17(s, 3H)

MS: 188, 186.

C. 4-Chloro-2,5-dimethoxybromomethylbenzene. N-Bromosuccinimide (22.2 g, 125 mmol) and 4-chloro-2,5-dimethoxytoluene were stirred in refluxing CCl4 (1079 mL). A solution of dibenzoyl peroxide in CCl4 (280 mg, 1.2 mmol, in 10 mL CCl4) was added in 4 portions over a 0.5 hour period. The reaction mixture was allowed to reflux overnight, or until 100% of the solid was on the surface of the CCl4. The solution was cooled to room temperature, filtered by suction in the hood, and the solvent was removed. The crude product was recrystallized from high boiling petroleum ether to give material suitable for the next step, yield 20.4 g, 68%, mp 99.5°–100.5° C.

IR: 1495, 1455 d, 1397

$^1$H-NMR: (300 MHz): 6.95(s, 2H), 4.55(s, 2H), 3.90 (s, 3H), 3.88(s, 3H)

MS: 268, 266, 264

Anal. Calcd. for $C_9H_{10}$)2BrCl: C, 40.71; H, 3.80; Br, 30.092; Cl, 13.352

Found: C, 40.67; H, 3.80; Br, 30.38, Cl, 12.90

D. 4-Chloro-2,5-dimethoxybenzaldehyde. A solution of hexamethylenetetramine (19.05 g, 136 mmol) and 4-chloro-2,5-dimethoxybromomethylbenzene (29.75 g, 112.1 mmol) in CHCl3 (119.3 mL) was refluxed for 10 min as a precipitate formed, then for 4 hours more. One-half of the solvent was removed, acetone (59.6 mL) was added, and the solution was then cooled in ice. The precipitate was collected and air-dried. The crude salt was isolated in quantitative yield and had the following physical date, mp 195°–200° C. (decomp).

TLC: (Acetone insoluble)
IR: 2970, 2795, 1500, 1210.

The salt was heated under reflux for 1 hour in 50% HOAc (178.8 mL). Water (172.8 mL) and concentrated HCl (42.9 mL) were added, and boiling was continued for 5 min more. On being cooled in an ice bath, the solution deposited pure aldehyde (6.4304 g, or 28–63%), mp 112°–114° C.

TLC: (Solvent B-) $R_f=0.65$ (fluorescent) (CHCl$_3$:pentane, 3:1) $R_f=0.77$ (fluorescent)
IR: 2970, 2795, 1500, 1210
UV: 217 (20281), 253 (13714), 340 (7340)
$^1$H-NMR: (300 MHz) 10.39(s, 1H), 7.38(s, 1H), 7.07(s,1H), 3.91(s,6H)
MS: 202, 200, 187, 185
Anal. Calcd. for C$_9$H$_9$ClO$_3$: C, 53.882; H, 4.522; Cl, 17.672.
Found: C, 53.74; H, 4.59; Cl, 17.67.

E. 3-(Carbethoxy)-4-(4'-chloro-2',5'-dimethoxyphenyl)-3-butenoic acid. Dried toluene (2.0 mL) was added to sodium hydride (2.26 g of a 50% oil dispersion which had been washed 4 times with low boiling petroleum ether, and twice with toluene) with stirring, under nitrogen, at room temperature. A catalytic amount of absolute ethanol (0.22 mL) was added to the gray solution, causing the evolution of gas. A warm solution of the aldehyde D. (3.8 g, 19.0 mmol), diethyl succinate (9.7 mL, 58.3 mmol) and toluene (25 mL) was added at a rate sufficient to maintain a reaction temperature of 40° C. (about 20 min). The addition funnel was then washed with toluene (5 mL). The mixture was stirred for 1 hour at 40° C., then acetic acid (4.3 mL), followed by water (9 mL) was cautiously added. The mixture was poured into a separatory funnel, followed by diethyl ether (40 mL) and 2N sodium carbonate (112 mL). The aqueous layer was separated, and acidified with IM hydrochloric acid (242 mL) to pH=2.0 (Congo Red) in an ice bath. The precipitate was collected, and the filtrate was extracted with diethyl ether. The diethyl ether was dried (MgSO$_4$), filtered, and the solvent was removed under reduced pressure. After TLC analysis, the precipitate and the material obtained from the ether extract were combined to provide 4.0 g (64%) of material which, though an oil, was suitable for the next step. A portion of the oil was subjected to preparative thin layer chromatography, followed by recrystallization in diethyl ether/pentane, providing material suitable for complete characterization, mp 152°–153° C.

TLC: (CHCl$_3$:pentane, 3:1) $R_f=0.0$ (Solvent B-) $R_f=0.58$
UV: 215 (sh) (20193), 263 (12399), 320 (9211)
$^1$H-NMR: (300 MHz) 7.95(s, 1H), 7.1(s, 1H), 6.9(s, 1H), 4.35(q, 2H), 3.85(s, 3H) 3.75(s, 3H), 3.5(s, 2H), 1.4(t, 3H)
MS: 330, 328, 286, 284, 197, 195
Anal. Calcd. for C$_{15}$H$_{17}$ClO$_6$: C, 54.80; H, 5.21
Found: C, 54.92; H, 5.33.

F. Ethyl 4-acetoxy-5,8-dimethoxy-6-chloro-naphthoate. The above acid (1.97 g, 6 mmol), acetic anhydride (3.4 mL), and sodium acetate 557 mg, 6.8 mmol) were stirred for 5 hours at 137° C. under nitrogen. The mixture was poured onto iced water. Sodium bicarbonate (12 mL of 1M) was added, and this solution was extracted with diethyl ether. The organic layer was dried (MgSO$_4$), filtered, and the solvent was removed under reduced pressure This provided 1.44 g (68% yield) of product. This material was recrystallized in methanol, mp 146.0°–147.3° C.

TLC: (CHCl$_3$:pentane, 3:1) $R_f=0.80$ (Solvent B-) $R_f=0.66$
IR: 1760, 1700, 1595, 1490, 1435, 1340, 1275, 1200
UV: 238 (53233), 294 (sh), 309 (7727), 328 (sh), 343 (9874)
$^1$H-NMR: 8.91(s, 1H), 7.81(s,1H), 6.87(s, 1H), 4.42(q, 2H), 4.01(s, 3H), 3.86(s, 3H), 2.38(s, 3H), 1.41(t, 3H).
Anal. Calcd. for C$_{17}$H$_{17}$ClO$_6$: C, 57.88; H, 4.86
Found: C, 57.86; H, 4.92.

The compound of Example 7 is useful as an intermediate in the synthesis of 11-deoxydaunomycin and analogues thereof which have utility as anticancer antibiotics.

The compound of Example 1, in particular, is useful as an antiviral agent, most particularly as an anti-HIV agent. Anti-HIV activity was determined as follows:

HIV-susceptible human T4 lymphocytes (CEM-V), with and without human immunodeficiency virus, were contained in three separate microculture plates. Various concentrations of the Example 1 compound were added, and the plates were incubated for seven days. During this time, infected, non-drug treated control cells were largely or totally destroyed by the virus. The number of remaining viable cells was utilized as a colorimetric end point. The results for the three plates are set forth below, wherein the percentage of cells surviving as a function of dosage of compound is indicated as "Response (%)".

| PLATE 1 | | | |
|---|---|---|---|
| INFECTED CULTURE | | UNINFECTED CULTURE | |
| Dose (μg/mL) | Response (%) | Dose (μg/mL) | Response (%) |
| $3.13 \times 10^{-6}$ | 23.6 | $3.13 \times 10^{-6}$ | 106.7 |
| $3.13 \times 10^{-5}$ | 23.2 | $3.13 \times 10^{-5}$ | 101.2 |
| $3.13 \times 10^{-4}$ | 12.6 | $3.13 \times 10^{-4}$ | 89.4 |
| $3.13 \times 10^{-3}$ | 11.8 | $3.13 \times 10^{-3}$ | 94.5 |
| $3.13 \times 10^{-2}$ | 11.5 | $3.13 \times 10^{-2}$ | 94.8 |
| $3.13 \times 10^{-1}$ | 9.9 | $3.13 \times 10^{-1}$ | 91.2 |
| $3.13 \times 10^{+0}$ | 18.1 | $3.13 \times 10^{+0}$ | 84.1 |
| $3.13 \times 10^{+1}$ | 56.2 | $3.13 \times 10^{+1}$ | 66.5 |

| PLATE 2 | | | |
|---|---|---|---|
| INFECTED CULTURE | | UNINFECTED CULTURE | |
| Dose (μg/mL) | Response (%) | Dose (μg/mL) | Response (%) |
| $9.91 \times 10^{-3}$ | 16.3 | $9.91 \times 10^{-3}$ | 111.9 |
| $3.13 \times 10^{-2}$ | 17.1 | $3.13 \times 10^{-2}$ | 104.0 |
| $9.90 \times 10^{-2}$ | 14.5 | $9.90 \times 10^{-2}$ | 107.3 |
| $3.12 \times 10^{-1}$ | 20.4 | $3.12 \times 10^{-1}$ | 112.5 |
| $9.87 \times 10^{-0}$ | 75.3 | $9.88 \times 10^{-1}$ | 113.3 |
| $3.12 \times 10^{+1}$ | 67.6 | $3.12 \times 10^{+0}$ | 119.7 |
| | | $9.87 \times 10^{+0}$ | 96.0 |
| | | $3.12 \times 10^{+1}$ | 87.8 |

| PLATE 3 | | | |
|---|---|---|---|
| INFECTED CULTURE | | UNINFECTED CULTURE | |
| Dose (μg/mL) | Response (%) | Dose (μg/mL) | Response (%) |
| $9.91 \times 10^{-3}$ | 18.5 | $9.91 \times 10^{-3}$ | 108.7 |
| $3.13 \times 10^{-2}$ | 23.2 | $3.13 \times 10^{-2}$ | 101.3 |
| $9.90 \times 10^{-2}$ | 16.0 | $9.90 \times 10^{-2}$ | 105.1 |
| $3.12 \times 10^{-1}$ | 24.0 | $3.12 \times 10^{-1}$ | 100.1 |

-continued

| PLATE 3 | | | |
|---|---|---|---|
| INFECTED CULTURE | | UNINFECTED CULTURE | |
| Dose (μg/mL) | Response (%) | Dose (μg/mL) | Response (%) |
| 9.87 × 10+0 | 101.4 | 9.88 × 10−1 | 102.9 |
| 3.12 × 10+1 | 78.7 | 3.12 × 10+0 | 102.1 |
| | | 9.87 × 10+0 | 85.2 |
| | | 3.12 × 10+1 | 81.3 |

While the Example 1 compound was active against HIV-infected cells in all three tests, the degree of protection (56.2% survival) at the Plate 1 maximum dose of 31.3 μg/mL corresponded with significant toxicity (66.5% survival) in the uninfected control cells. In Plates 2 and 3, the dosage of drug, 9.87 μg/mL, which provided maximum protection from HIV infection (75.3% survival, Plate 2; 101.4% survival, Plate 3) was not toxic or only slightly toxic to uninfected cultures (96.0% survival Plate 2; 85.2% survival Plate 3).

The compounds can be administered to warm-blooded animals perorally, parenterally, topically or the like in customary dosage unit compositions. For pharmaceutical use, the compounds of the invention may be taken up in any pharmaceutically acceptable carrier, such as solutions, suspensions, tablets, capsules, ointments, elixirs and injectable compositions and the like. The compounds may be administered to subjects suffering from viral infection, e.g. HIV infection. A pharmaceutical composition adapted for administration to obtain an antiviral effect, comprises an antivirally effective amount of a compound of formula 1 and a pharmaceutical carrier. An antiviral effective amount is any amount of compound which is sufficient to provide a plasma concentration of at least about 10 μg/ml in the infected individual.

The dosage of active agent administered can vary over a wide range, e.g., 0.1 mg to 10 g daily, depending upon the mode of administration, the size and weight of the subject, and whether the treatment is prophylactic or therapeutic. The actual dosage also depends upon the nature and severity of the infection, the disease stage, and when administered systemically, the size and weight of the infected subject.

The present invention may be embodied in other specific forms without departing from the spirit or essential attributes thereof and, accordingly, reference should be made to the appended claims, rather than to the foregoing specification, as indicating the scope of the invention.

I claim:

1. A method of treating a mammal for viral infection comprising administering to such a mammal a compound according to the formula:

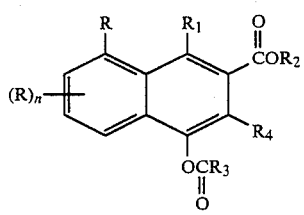

wherein
n is 1 or 2;
R is methoxy or chloro, or combinations thereof;
$R_1$ is hydrogen or lower alkyl;
$R_2$ is methyl or ethyl;
$R_3$ is methyl or ethyl; and
$R_4$ is hydrogen or methyl.

2. A pharmaceutical composition adapted for administration to obtain an antiviral effect comprising a pharmaceutical carrier and an antiviral effective amount of compound of the formula:

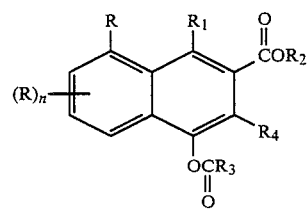

wherein
n is 1 or 2;
R is methoxy or chloro, or combinations thereof;
$R_1$ is hydrogen or lower alkyl;
$R_2$ is ethyl;
$R_3$ is methyl or ethyl; and
$R_4$ is hydrogen or methyl.

3. A method according to claim 1 wherein the compound is of the formula:

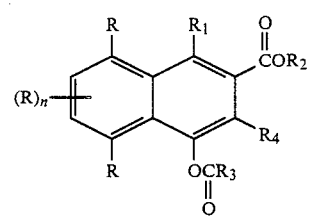

wherein
m is 0 or 1;
R is methoxy or chloro, or combinations thereof;
$R_1$ is hydrogen or lower alkyl;
$R_2$ is methyl or ethyl;
$R_3$ is methyl or ethyl; and
$R_4$ is hydrogen or methyl.

4. A method according to claim 1 wherein $R_2$ is ethyl.

5. A method according to claim 1 wherein each R is methoxy.

6. A method according to claim 4 wherein each R is methoxy.

7. A method according to claim 6 wherein the compound is ethyl 4-acetoxy-5,8-dimethoxy-2-naphthoate.

8. A method according to claim 6 wherein the compound is ethyl 4-acetoxy-5,6,8-trimethoxy-2-naphthoate.

9. A method according to claim 6 wherein the compound is ethyl 1-methyl-4-acetoxy-5,8-dimethoxy-2-naphthoate.

10. A method according to claim 4 wherein the compound is ethyl 4-acetoxy-5,8-dimethoxy-6-chloro-2-naphthoate.

11. A composition according to claim 2 wherein the compound is of the formula:

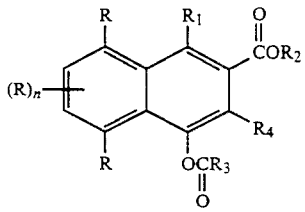

wherein m is 0 or 1;

R is methoxy or chloro, or combinations thereof;

$R_1$ is hydrogen or lower alkyl;

$R_2$ ethyl;

$R_3$ is methyl or ethyl; and $R_4$ is hydrogen or methyl.

12. A composition according to claim 2 wherein each R is methoxy.

13. A composition according to claim 11 wherein each R is methoxy.

14. A composition according to claim 13 wherein the compound is ethyl 4-acetoxy-5,8-dimethoxy-2-naphthoate.

15. A composition according to claim 13 wherein the compound is ethyl 4-acetoxy-5,6,8-trimethoxy-2-naphthoate.

16. A compound according to claim 13 wherein the compound is ethyl 1-methyl-4-acetoxy-5,8-dimethoxy-2-naphthoate.

17. A composition according to claim 11 wherein the compound is ethyl 4-acetoxy-5,8-dimethoxy-6-chloro-2-naphthioate.

* * * * *

UNITED STATES PATENT AND TRADEMARK OFFICE
CERTIFICATE OF CORRECTION

PATENT NO. : 4,975,463

DATED : December 4, 1990

INVENTOR(S) : James L. Bloomer

It is certified that error appears in the above-identified patent and that said Letters Patent is hereby corrected as shown below:

Col. 2, l. 65, insert a hyphen before and after "carbethoxy"; Col. 3, l. 20, between "5" and "8" change the period to comma (5,8); Col. 3, l. 26, insert --(-- before "mL"; Col. 3, l. 48, insert commas between "4" and "(" and between ")" and "3"; Col. 3, l. 63, insert --:-- after "(CDCl$_3$)"; Col. 4, l. 21, insert a hyphen between "dimethoxy" and "2"; Col. 6, l. 13, change "4" to --2--; Col. 6, l. 30, insert a hyphen between "4" and "Chloro"; Col. 6, l. 62, change ")" to --0--; Col. 7, l. 13, insert --)-- after "63%"; Col. 7, l. 66, insert --(-- before "557"; Col. 8, l. 56, after the first occurrence of "10" change the "-" to --+--; Claim 2 at col. 10, l. 7, insert --a-- after "of"; Claim 3 at col. 10, l. 35, after "(R)" change "n" to --m--; Claim 11 at col. 11, l. 5, after "(R)" change "n" to --m--; and Claim 11 at col. 11, l. 16,

UNITED STATES PATENT AND TRADEMARK OFFICE
CERTIFICATE OF CORRECTION

PATENT NO. : 4,975,463

DATED : December 4, 1990

INVENTOR(S) : James L. Bloomer

It is certified that error appears in the above-identified patent and that said Letters Patent is hereby corrected as shown below:

insert --is-- between "$R_2$" and "ethyl".

Signed and Sealed this

Twenty-ninth Day of December, 1992

Attest:

DOUGLAS B. COMER

Attesting Officer

Acting Commissioner of Patents and Trademarks